(12) United States Patent
Allen (10) Patent No.: US 8,025,625 B2
(45) Date of Patent: Sep. 27, 2011

(54) SENSOR WITH ELECTROMAGNETICALLY COUPLED HERMETIC PRESSURE REFERENCE

(75) Inventor: Mark G. Allen, Atlanta, GA (US)

(73) Assignee: CardioMEMS, Inc., Atlanta, GA (US)

( * ) Notice: Subject to any disclaimer, the term of this patent is extended or adjusted under 35 U.S.C. 154(b) by 84 days.

(21) Appl. No.: 11/402,439

(22) Filed: Apr. 12, 2006

(65) Prior Publication Data

US 2006/0241354 A1    Oct. 26, 2006

Related U.S. Application Data

(60) Provisional application No. 60/670,549, filed on Apr. 12, 2005.

(51) Int. Cl.
*A61B 5/00* (2006.01)

(52) U.S. Cl. .......................... 600/561; 73/754; 600/300

(58) Field of Classification Search .................. 600/300, 600/564, 561; 128/903; 73/754
See application file for complete search history.

(56) References Cited

U.S. PATENT DOCUMENTS

| | | | |
|---|---|---|---|
| 4,315,974 A * | 2/1982 | Athearn et al. | 429/181 |
| 5,963,012 A * | 10/1999 | Garcia et al. | 320/106 |
| 6,579,235 B1 | 6/2003 | Abita et al. | |
| 6,939,299 B1 * | 9/2005 | Petersen et al. | 600/398 |
| 7,059,195 B1 * | 6/2006 | Liu et al. | 73/753 |
| 7,075,160 B2 * | 7/2006 | Partridge et al. | 257/414 |
| 2001/0001311 A1 | 5/2001 | Park et al. | |
| 2002/0151816 A1 * | 10/2002 | Rich et al. | 600/547 |
| 2006/0047205 A1 | 3/2006 | Ludomirsky | |
| 2006/0174712 A1 * | 8/2006 | O'Brien et al. | 73/756 |

FOREIGN PATENT DOCUMENTS

| | | |
|---|---|---|
| EP | 0 897 690 A | 2/1999 |
| WO | WO 99/56614 A1 | 11/1999 |

* cited by examiner

*Primary Examiner* — Max Hindenburg
*Assistant Examiner* — Renee Danega
(74) *Attorney, Agent, or Firm* — Ballard Spahr LLP

(57) ABSTRACT

An electromagnetically coupled hermetic chamber includes a body defining a hermetic chamber. A first conductive structure is disposed within the hermetic chamber, and a second conductive structure is attached to the body outside of the hermetic chamber. The first conductive structure is electromagnetically coupled to the second conductive structure without direct electrical paths connecting the first and second conductive structures. Thus the first conductive structure can be coupled to external electronics without the need for electrical feedthroughs or vias that could compromise the integrity of the hermetic chamber.

30 Claims, 8 Drawing Sheets

SENSOR WITH ELECTROMAGNETICALLY COUPLED HERMETIC PRESSURE REFERENCE

CROSS-REFERENCE TO RELATED APPLICATIONS

This application is entitled to the filing date of provisional U.S. patent application Ser. No. 60/670,549, filed Apr. 12, 2005.

FIELD OF THE INVENTION

The present invention relates to sensors comprising hermetic packaging that eliminates the need for electrical feedthroughs, and sensors configured utilizing the same, all of which are intended to perform reliably in harsh and biological environments.

BACKGROUND OF THE INVENTION

Over the past 20 years, advances in the field of microelectronics have enabled the realization of microelectromechanical systems (MEMS) and corresponding batch fabrication techniques. These developments have allowed the creation of sensors and actuators with micrometer-scale features. With the advent of the above-described capability, heretofore implausible applications for sensors and actuators are now significantly closer to commercial realization.

In parallel, much work has been done in the development of pressure sensors. Pressure sensors are disclosed, for example, in U.S. Pat. No. 6,111,520, issued Aug. 29, 2000; U.S. Pat. No. 6,278,379, issued Aug. 21, 2001; U.S. Pat. No. 6,855,115, issued Feb. 15, 2005; U.S. patent application Ser. No. 10/054,671, filed Jan. 22, 2002; U.S. patent application Ser. No. 10/215,377, filed Aug. 7, 2002; U.S. patent application Ser. No. 10/215,379, filed Aug. 7, 2002; U.S. patent application Ser. No. 10/943,772, filed Sep. 16, 2004; U.S. patent application Ser. No. 11/157,375, filed Jun. 21, 2005; and U.S. patent application Ser. No. 11/314,046 filed Dec. 20, 2005, all of which are incorporated herein by reference.

In particular, absolute pressure sensors, in which the pressure external to the sensor is read with respect to an internal pressure reference, are of interest. The internal pressure reference is a volume within the sensor, sealed, which typically contains a number of moles of gas (the number can also be zero, i.e. the pressure reference can be a vacuum, which can be of interest to reduce temperature sensitivity of the pressure reference as known in the art). The external pressure is then read relative to this constant and known internal pressure reference, resulting in measurement of the external absolute pressure. For stability of the pressure reference and assuming the temperature and volume of the reference are invariant or substantially invariant, it is desirable that the number of moles of fluid inside the reference does not change. One method to approach this condition is for the reference volume to be hermetic.

The term hermetic is generally defined as meaning "being airtight or impervious to air." In reality, however, all materials are, to a greater or lesser extent, permeable, and hence specifications must define acceptable levels of hermeticity. Acceptable level of hermeticity is therefore a fluid ingress or egress rate which does not change the pressure in the internal reference volume (a.k.a. pressure chamber) by an amount large compared with the pressure of interest being measured over the accumulated time over which the measurements will be taken. An amount large compared with the pressure of interest should be construed to mean a change in the internal reference volume that is less than 10 percent, preferably less than 5 percent, and most preferably less than 1 percent of the external pressure being sensed. In many biological applications, an acceptable pressure change in the pressure chamber is on the order of 0.5-5 mm Hg/year.

The pressure reference is typically interfaced with a sensing means that can sense deflections of boundaries of the pressure reference when the pressure external to the reference changes. A typical example would be bounding at least one side of the pressure reference with a deflectable diaphragm or plate and measuring the deflection of the diaphragm or plate by use of, among other techniques, a piezoresistive or a capacitance measurement. If the deflection of the diaphragm or plate is sufficiently small, the volume change of the pressure reference does not substantially offset the pressure in the pressure reference.

These approaches may require an electrical feedthrough to the hermetic environment (e.g., to contact electrodes inside the hermetic pressure reference) for connection to outside electronics to buffer or transmit the signal. Alternatively, electronics may be incorporated within the reference cavity, requiring power to be conducted into the hermetic environment. To maintain stability of the pressure reference, these seals should also be hermetic, resulting in the necessity to develop a feedthrough technology for electrical contacts through the cavity walls. As is known in the art, such feedthrough locations are typically sites for failure of hermeticity. This problem is further exacerbated when miniaturizing the sensor, since the total volume of material available for hermetic sealing shrinks proportionally and the reliability of the feedthrough is also greatly reduced. In the limit of ultraminiaturized sensors, such as those producible using microelectromechanical systems (MEMS) technology, it would be desirable to eliminate these feedthroughs in their entirety while maintaining the ability to supply power and/or exchange information with the circuitry inside the hermetic pressure reference.

Thus a need exists for sensors comprising hermetic cavities which maintain electrical communication with the ambient without physically breaching the hermetic cavity.

SUMMARY OF THE INVENTION

The present invention is a hermetic cavity in which information and/or energy can be transmitted through the walls of the cavity without the need to form a physical breach of the wall of the cavity. A particularly useful embodiment of the invention is a sensor that is comprised of a sensor body which defines a hermetic cavity. All sensing elements associated with the sensor are located within the hermetic cavity and therefore are hermetically sealed from the surrounding environment, thereby reducing drift and instability of the sensor. Electrical communication between the sensing elements and electronics external to the hermetic chamber is accomplished by means of electromagnetic coupling between two complementary conductors located on opposite sides of at least one wall defining the hermetic cavity.

Additional circuitry, e.g., sensing circuitry, can be placed in electrical communication or integral with the conductor inside the hermetic cavity and electrically biased when the conductor inside the hermetic cavity (a.k.a., the internal conductor) is energized. Direct electrical contact, e.g., by means of electrical feedthroughs, can be established between the conductor which is external to the hermetic cavity (a.k.a., the external conductor) and attachment means on the external wall of the sensor in order to connect the device to further electronics.

Sensors of the present invention are entirely self-packaged and maintain electrical communication with the surrounding environment without the need for electrical feedthroughs breaching the hermetic cavity. Elimination of feedthroughs into the hermetic cavity increases reliability and durability of the sensor by eliminating a feature that is frequently cited as a point of failure of hermeticity in such devices. The sensor can be fabricated using high-purity, hermetic and biocompatible materials, e.g., ceramics, metals and polymers. If ceramics are used to construct the sensor body defining the hermetic cavity, the ceramic substrates can be fused together so that there is no interface of material remaining where the substrates have been joined to create a cavity. This eliminates any material interface in the sensor body that could become the site of a potential leak path into the hermetic cavity and, consequently, increases the reliability and durability of the sensor. Alternatively, anodic or eutectic bonding techniques can be utilized to create the hermetic cavity. Furthermore, sensors of the present invention can be manufactured using microelectromechanical systems (MEMS) fabrication techniques, which allow creation of a device that is small, accurate, precise, durable, robust, biocompatible, and insensitive to changes in body chemistry or biology.

The present invention further comprises a device that can be incorporated into harsh and biological environments. One example of such an environment is a medical lead or catheter implanted, acutely or chronically, into the human body. The present invention is disclosed in the context of a pressure sensor, but it should be understood that the packaging and communication scheme can be utilized in the creation of any device where hermeticity is desirable. Communication between the sensor and another device can be established by, e.g., electrical feedthroughs terminating in bond pads on the exterior of the sensor body or wires protruding from the sensor body, either of which are configured so that they are in electrical contact with and able to electrically bias the external conductor.

In one embodiment of the invention, inductive coupling is utilized to establish electrical communication with components residing inside the hermetic cavity. The complementary conductors comprise at least two inductors. In a further embodiment, the inductors comprise planar wire spiral inductors. Although the invention is illustrated by means of inductive coupling through the walls of the hermetic chamber, it should be recognized that alternative means of coupling, including but not limited to capacitive, distributed capacitive/inductive, optical, and combinations thereof, may also be utilized.

In another embodiment of the invention, the hermetic cavity is further configured to be sensitive to a selected range of pressure. The pressure cavity (i.e., this pressure-sensitive hermetic cavity) further comprises a capacitor configured so that the characteristic capacitance value of the capacitor indicates a physical state, or changes in a physical state, within a patient. The electrodes of the capacitor are substantially planar and are arranged substantially parallel to and spaced apart from one another. The pressure cavity has at least one deflectable region in mechanical communication with at least one of the capacitor electrodes. In this embodiment, the capacitor and inductor are realized through mutually-imposed, planar spiral inductor coils located on opposite sides of the pressure cavity with at least a portion of one of the planar spiral coils fixed to the deflective region. The inductance and capacitance of the circuit are distributed across the area of the mutually-imposed coils. The spiral coils can, optionally, terminate in electrodes. This feature increases the capacitance of the circuit and allows the resonant frequency of the circuit to be tuned by varying the size of the electrodes. Another mutually-imposed, planar spiral inductor coil is located external to the pressure cavity in magnetic proximity to the internal spiral inductor coils. This external inductor coil is isolated from the surrounding environment by coating it with a suitable polymer or encasing it in a ceramic material. In either case, wires or electrical feedthroughs terminating in bond pads are provided so that connection of the sensor to other electronics can be established.

In another embodiment, the hermetic cavity is further configured to be sensitive to a selected range of pressure. The pressure cavity further comprises a capacitor configured so that the characteristic capacitance value of the capacitor indicates a physical state, or changes in a physical state, within a patient. The electrodes of the capacitor are substantially planar and are arranged substantially parallel to and spaced apart from one another. The pressure cavity has at least one deflectable region in mechanical communication with at least one of the capacitor electrodes. In a further embodiment, the LC circuit is realized through connecting the capacitor to a three-dimensional inductor coil. Another inductor coil is located external to the pressure cavity and in magnetic proximity to the internal coil. This external inductor coil is isolated from the surrounding environment by coating it with a suitable polymer or encasing it in a ceramic material. In either case, wires or electrical feedthroughs terminating in bond pads are provided so that connection of the sensor to remote electronics can be established.

In yet another embodiment, a wired sensor further comprises on-board (i.e., within the sensor package) electronics, e.g., a silicon chip bearing electronics. This embodiment has the advantage of reduced sensitivity to external electromagnetic effects introducing spurious signals on the leads of the previous embodiments, especially if such leads are long. The variable capacitive element and the on-board electronics can be maintained in separate cavities in electrical communication with one another by opposed inductor coils located on either side of a middle substrate. Feedthroughs establishing electrical communication between the interior of the second chamber and the ambient are provided in this case. Such feedthroughs are configured so that moisture does not affect the electronics over the life of the sensor and, optionally, are hermetic.

DETAILED DESCRIPTION OF THE INVENTION

Figure 1:
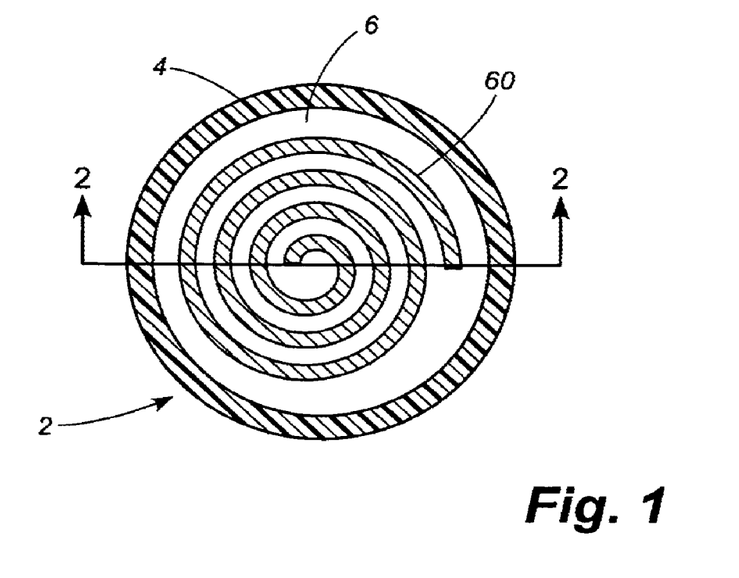
FIG. 1 is a cross-sectional view of a sensor with an electromagnetically-coupled hermetic cavity according to a disclosed embodiment of the present invention, taken along line 1-1 of FIG. 2.
Figure 2:
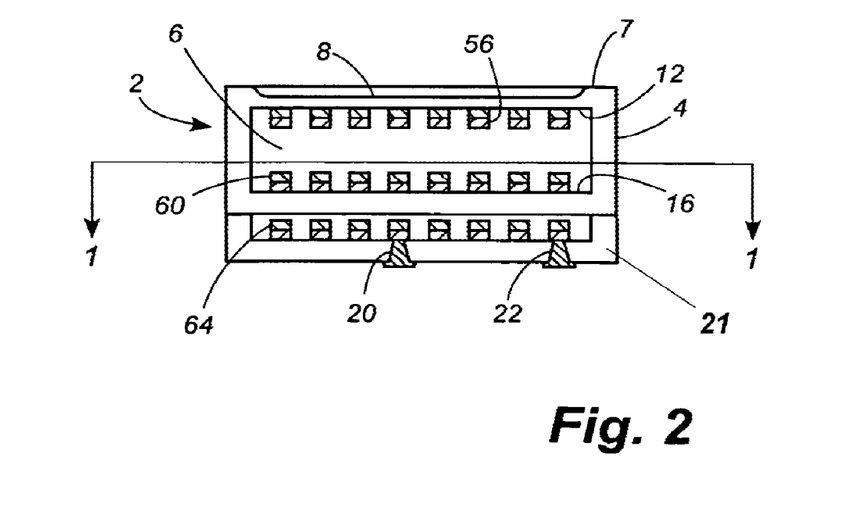
FIG. 2 is a cross-sectional view taken along line 2-2 of FIG. 1.

Referring now to the drawings, in which like numerals indicate like elements throughout the several views, FIGS. 1 and 2 illustrate a sensor 2 comprising a sensor body 4. The sensor body 4 is formed from electrically insulating materials, particularly biocompatible ceramics and polymers. Suitable ceramic materials include glass, fused silica, sapphire, quartz, or silicon. Suitable polymeric materials include polyimide, liquid crystal polymer (LCP), urethane, polyester, Teflon, FEP, PTFE, polyamide and silicone rubber, treated or configured such that the permeation of these materials is reduced to a level such that leakage rates are commensurate with the definition of hermeticity provided herein. Additionally, the sensor 2 can incorporate radiopaque features to enable fluoroscopic visualization during placement within the body.

The sensor body 4 defines a hermetic chamber 6. One of the walls 7 defining the hermetic chamber 6 comprises a deflectable region 8 configured to deflect under a physiologically relevant range of pressure. In one embodiment, the wall 7 of the pressure-sensitive hermetic chamber 6 is thinned relative to other walls of the sensor body 4 to form the deflectable region 8.

Within the hermetic chamber 6 of the sensor 2 is a first conductive structure comprising a pair of planar spiral coils 56 and 60 disposed in parallel, spaced-apart relation. The spiral coils 56 and 60 are not DC coupled, i.e., not connected by a conductive trace. The spiral coils 56 and 60 comprise a distributed LC circuit. In a distributed LC circuit, the inductance and capacitance are distributed across the entire planar spiral circuit. The first planar spiral coil 56 is fixed to the upper wall 7 of the hermetic chamber 6. The second planar spiral coil 60 is oppositely disposed to the first planar spiral coil 56 and fixed to a lower wall 16 of the hermetic chamber 6.

Located on the opposite side of the lower wall 16 is a third planar spiral coil 64. The third planar spiral 64 is disposed outside the hermetic chamber 6 and located in proximity to the first conductive structure 56, 60. The third planar spiral coil 64 is embedded in a housing 21 of ceramic or polymeric material so as to isolate the coil 64 from the surrounding environment and to stabilize it with respect to the second planar spiral coil 60. A first metal trace 20 and a second metal trace 22 extend from opposing ends of the third planar spiral coil 64 to the exterior of the housing 21. The metal traces 20, 22 can be further connected to a bond pad (not shown) on the exterior of the housing 21 that will allow for other electronics (not shown) to be placed in electrical communication with the sensor 2. Alternatively, the metal traces 20, 22 cart further comprise wires extending from the sensor package to which other electronics (not shown) can be placed in electrical communication with the sensor 2.

When the third coil 64 is energized by an external AC signal generator, the three planar spiral coils 56, 60, and 64, respectively, act as inductors. The circuit contained within the hermetic chamber 6 exhibits the electrical characteristics associated with a standard inductor-capacitor (LC) circuit. In the embodiment discussed herein, the LC circuit is in part distributed as known in the art. If a current is induced in the LC circuit at a particular frequency known in the art as the resonant frequency of the circuit, the resultant energy will be maximally shared between the inductor and capacitor. The result is an energy oscillation that will vary at a specific frequency. This frequency is termed the "resonant frequency" of the circuit, and it can easily be calculated from the circuit's inductance and capacitance. Therefore, a change in capacitance or inductance will cause the resonant frequency to shift higher or lower, depending upon the change in the value of variable element(s). Further, the value of the resonant frequency can be inferred from the electrical characteristics of external coil 64, e.g., by monitoring the impedance of coil 64 as a function of frequency as known in the art. Since mechanical deflection of the deflective region 8 alters the value of the characteristic distributed capacitance and inductance and therefore the resonant frequency, and since the deflection of the deflective region 8 is dependant on the external pressure, detection of this resonant frequency using the coil 64 therefore allows determination of the pressure in which the sensor 2 is embedded without the need for direct electrical connection with the circuitry inside the hermetic chamber 6.

A disclosed method for fabricating the sensor 2 depicted in FIGS. 1 and 2 is based on the micromachining of at least two substrates that are subsequently brought into contact and fused together. The manufacturing process described herein and illustrated in FIGS. 3-18 comprises a series of etching, patterning, and deposition processes to create depressions and planar spiral coils on the surfaces of the substrates. More specifically, a first substrate is subjected to a series of processes to create a local depression of known depth and to deposit a planar spiral coil at the bottom of the depression. Next, a second substrate is subjected to similar processing as the first substrate to create a complementary planar spiral coil whose overall footprint and in-plane position correspond to the footprint and in-plane position of the planar spiral coil on the first substrate. Creation of a depression in the surface of the second substrate is optional and depends on the desired final configuration of the sensor. Optionally, the first substrate is then subjected to additional processing on the side of the substrate opposite the previously formed planar spiral coil to deposit a third planar spiral coil whose overall footprint and in-plane position correspond to the footprint and in-plane position of the planar spiral coil previously deposited on the first substrate. Alternatively, a third substrate is subjected to an identical series of preparatory steps as the first two substrates and presents a planar spiral coil that does not protrude past the uppermost surface of the substrate (i.e., it is recessed) and whose overall footprint and in-plane position corresponds to the footprint and in-plane position of the planar spiral coil on the first substrate when the substrates are brought into contact. The configuration of the planar spiral coils can be altered to provide for a variety of geometries as manufacturing and/or performance advantages may dictate. The first two substrates are brought into face-to-face contact, forming the hermetic chamber, and, optionally, a third substrate corresponding to the housing 21 is then brought into intimate contact with the back side of first substrate. Alternatively, if the third set of planar coils are plated on the back side of the first substrate, electrical contact with the coils are provided for and the coils are isolated from the surrounding environment by a polymer or ceramic material. The components are aligned as shown in FIG. 1. The substrates form a temporary bond because of the presence of Van der Waals forces. The planar spiral coils contained within a chamber formed upon imposition of the first and second substrates are separated by a gap of known value, i.e., the difference between the sum of the depths of the recessed region and the sum of the thicknesses of the electrodes. A laser is then used to excise the sensor into its final overall dimensions from the at least two-substrate stack.

The laser cutting operation fuses the substrates, hermetically sealing the sensor and trapping air or any other desirable gas in the hermetic cavity of the sensor, or creating a vacuum within the hermetic cavity of the sensor. In one example, a $CO_2$ laser operating at a peak wavelength of ten microns is used to hermetically seal and to reduce the sensor to its final size. The laser energy is confined to a precise heat effect zone where the substrates are fused, eliminating any material interface between the original substrates.

The resulting sensor presents three mutually-arranged planar spiral coils that, through inductive coupling, are capable of sensing ambient pressure. More particularly, a change in environmental pressure causes the deflective region to be displaced, and the capacitor electrode fixed to that region moves with respect to the coil formed on the first substrate. Thus, the electrical characteristics (e.g., energy loss, phase change) of the LC circuit located within the hermetic chamber are altered. When an external AC signal source is placed in connection with the third coil, electromagnetic coupling supplies energy to the first two coils, which are located in magnetic proximity to the third coil. The resulting electromagnetically-coupled circuit, i.e., the three mutually-imposed planar spiral coils, will change predictably in response to external changes in pressure.

The manufacturing of the sensor 2 depicted in FIGS. 1 and 2 from the substrate (a.k.a. wafer) level to the final device is described in greater detail below. For clarity, the manufacture of the sensor 2 is described on a single-sensor basis, although it will be understood that multiple sensors are preferably created simultaneously on the substrate in a batch process to increase manufacturing efficiency.

The lower substrate is processed to create a recessed region in its surface and planar spiral coils at the bottom surface of the recessed region. Creation of a recessed region with known geometry comprises the steps of (i) depositing and patterning a mask at the surface of the wafer, (ii) etching the wafer material through openings in the mask, and (iii) removal of the mask.

Figure 3:
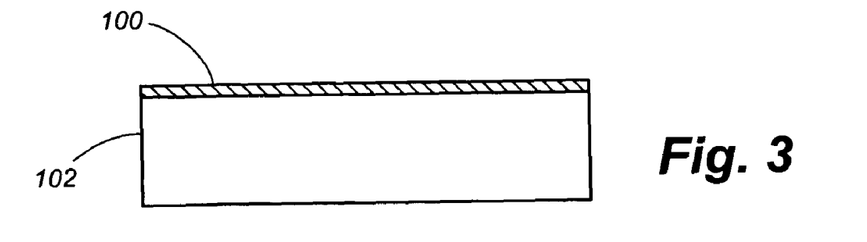
FIGS. 3-18 are schematic representation of the steps in manufacturing the sensor of FIGS. 1 and 2.
Figure 4:
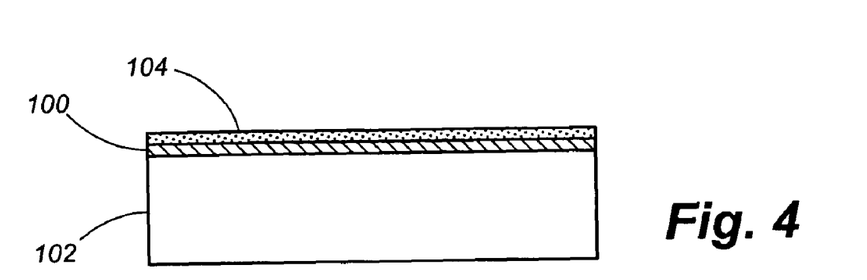
Figure 5:
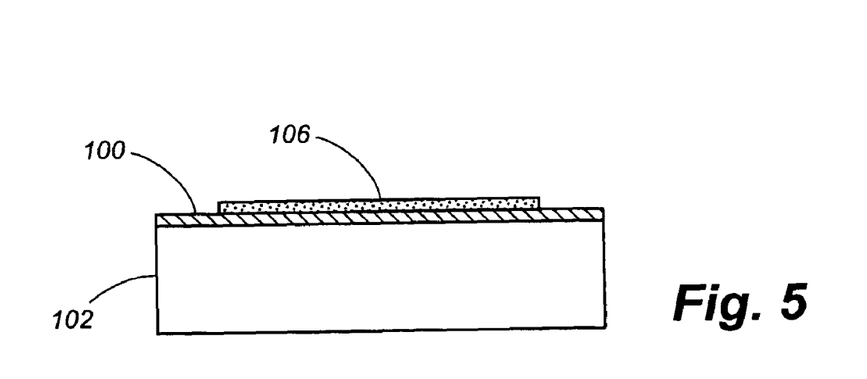

One method for creating the desired recessed region is depicted in FIGS. 3-10 and described as follows: Referring first to FIG. 3, a seed layer 100 is deposited on the surface of a fused silica substrate 102 and comprises a 1000-2000 Angstrom layer of Cr/Cu. As can be seen in FIG. 4, a layer 104 of photoresist is formed atop the seed layer 100. Then, as shown in FIG. 5, photolithographic techniques are used to reduce the photoresist layer to provide an island 106 of photoresist that defines the perimeter of a desired recessed region. This photoresist is approximately 5-10 micrometers thick, depending on the desired height of the metal to be plated in the subsequent step.

Figure 6:
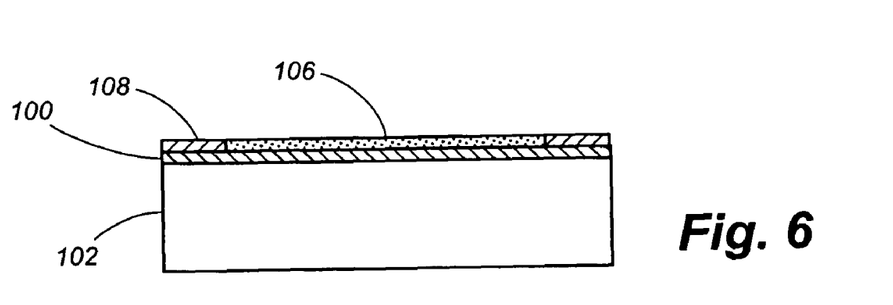
Figure 7:
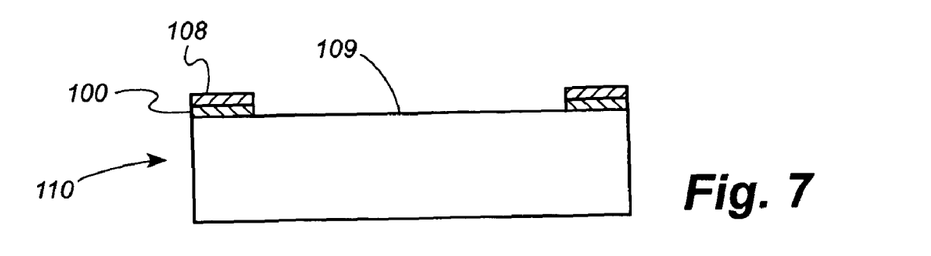
Figure 8:
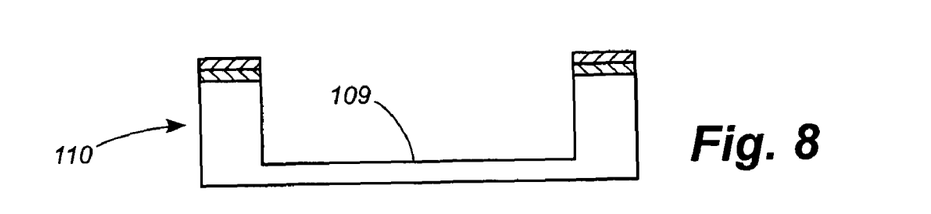
Figure 9:
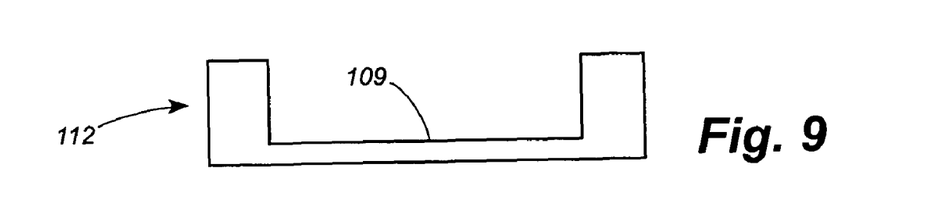

Next, as shown in FIG. 6, a metal (e.g., Ni) is plated to a selected height, in the range of 5-10 micrometers in the present example, to form a second mask 108. Then, as shown in FIG. 7, the photoresist and underlying seed layer are removed via selective etchants and solvents to expose the underlying substrate 102 in a central region 109, thereby forming a masked substrate 110. Next, the masked substrate 110 is subjected to further selective etchants such as hydrofluoric acid solutions, to remove the fused silica in the exposed central region 109 to a desired depth, e.g., 70 micrometers, as shown in FIG. 8. Then, the second mask 108 and remaining seed layer 100 are removed with selective etchants and solvents to form the etched substrate 112 with recessed region 109, as shown in FIG. 9.

Figure 10:
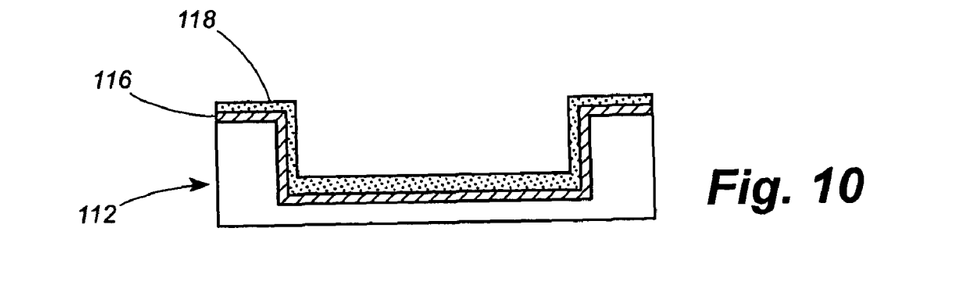
Figure 11:
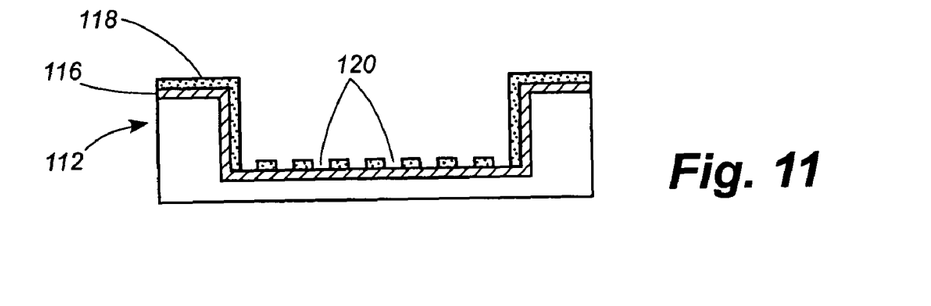
Figure 12:
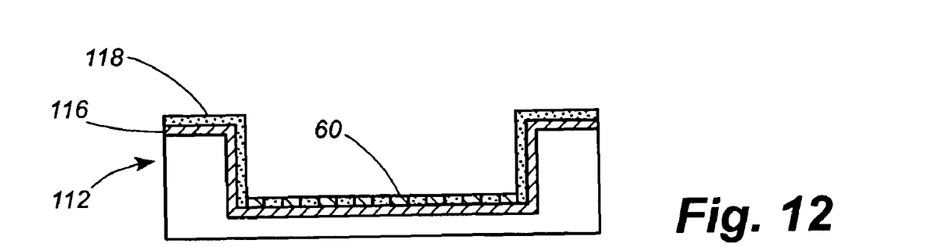

Now, thick planar spiral coils are created in the bottom of the recessed region 109 of the etched substrate 112. To this end, as shown in FIG. 10, a second seed layer 116 and second photoresist layer 118 are deposited on the etched substrate 112. The photoresist layer 118 is 25-35 micrometers in height, depending on the desired height of the planar coil created in the next step. Then, photolithographic techniques are used to etch away material to create recesses 120 in the photoresist layer, thereby forming a mold defining the desired planar coil pattern, as shown in FIG. 11. A thick metal planar spiral 60 is then formed by electroplating Cu to a height of 25-35 micrometers on the exposed seed layer 116, as shown in FIG. 12. The photoresist 118 and seed layer 116 underlying the photoresist are then removed via selective etchants and solvents.

Figure 13:
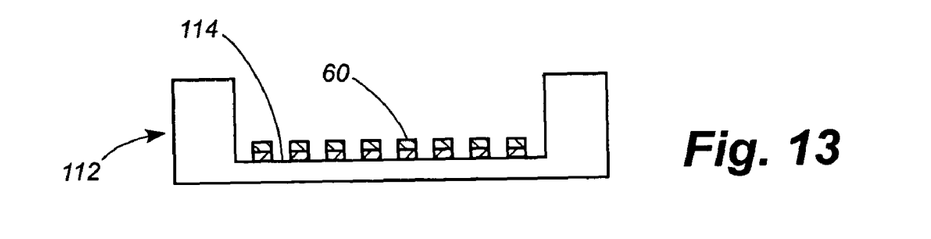

At this point, as depicted in FIG. 13, the etched lower substrate 112 is patterned with a recessed region 114 etched into its upper surface, and the base of the recessed region 114 contains a planar spiral coil 60 of known thickness. The difference between the height of the upper surface of the planar spiral, HI, and depth D} of the recessed region 114 in lower substrate 112, is substantially constant (excepting for inherent variations in the substrate and patterned metal), and these dimensions are known with great precision, i.e. fractions of micrometers.

Figure 14:
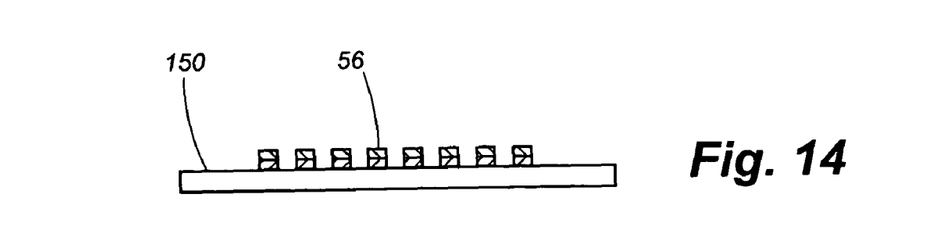

Referring now to FIG. 14, an upper substrate 150 is provided and a second planar spiral 56 is created using the same photolithographic and metal deposition processes as those described for the lower substrate 112.

Figure 15:
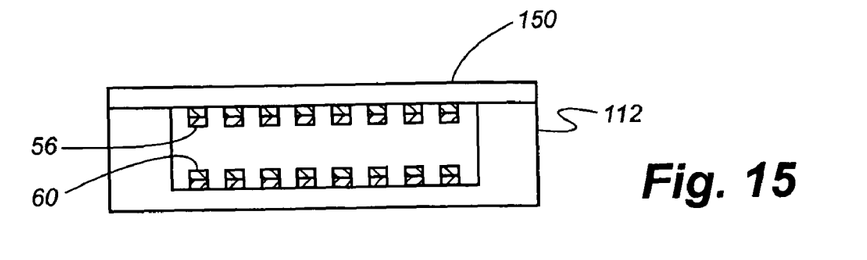
Figure 16:
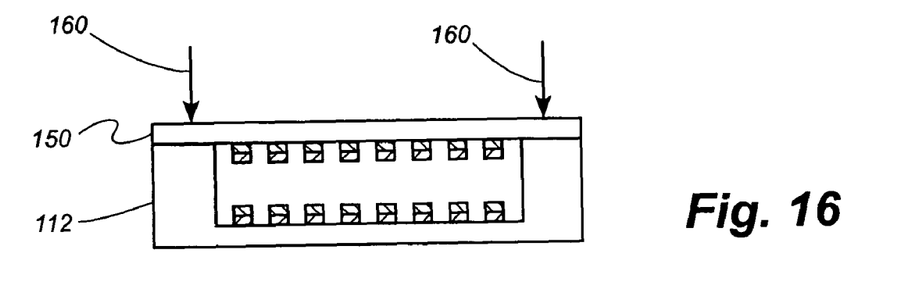

The substrates 112, 150 are then aligned, subjected to bonding, and reduced to the final overall dimension of the sensor as shown in FIG. 1 according to the following description: Both the upper and lower substrates 112, 150 are prepared for assembly, e.g., by cleaning The patterned surfaces of the substrates are faced and aligned so that the planar spiral coils 56, 60 created in each substrate are positioned directly on top of one another. The two substrates 112, 150 are brought together and placed in intimate physical contact, as shown in FIG. 15. A temporary bond is formed because of Van der Waals forces existing between the two substrates. As previously described, a gap is maintained between the first planar spiral coil 56 and the second planar spiral coil 60 where the distance between the planar spiral coils is precisely known. Referring to FIG. 16, using a $CO_2$ laser, indicated by the arrows 160, the sensor is reduced to its final dimensions. The laser cutting process also fuses the upper and lower substrates 112, 150 substantially seamlessly. The pressure cavity body 152 resulting from the above steps is depicted in FIG. 17.

Figure 17:
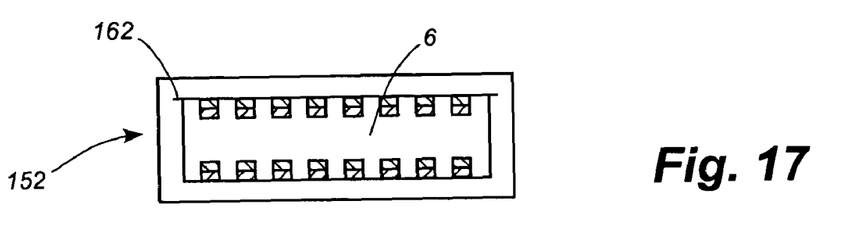
Figure 18:
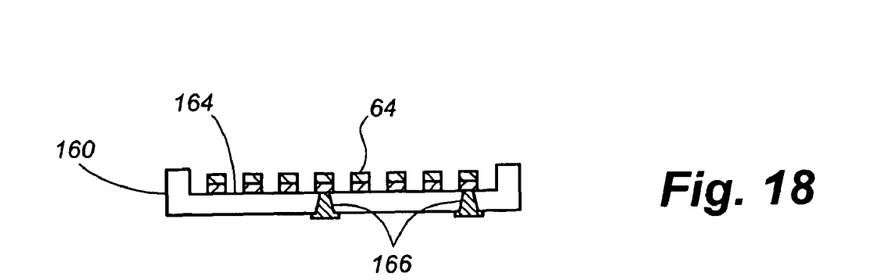

With further reference to FIG. 17, the power of the $CO_2$ laser is controlled such that heat damage to the internal components is avoided. Consequently it is possible that some vestige of a seam 162 may remain between the upper and lower substrates 112, 150. So long as the outer periphery of the pressure cavity body 152 is completely fused, the interior chamber 6 will be hermetic.

At some point during the process outlined above, the third planar spiral coil is provided. This feature can be achieved two ways: (i) by providing a third substrate with a third planar spiral coil recessed within a depression and adding this substrate to the two wafer stack before they are fused or (ii) by depositing a third planar spiral coil on the bottom of the first substrate 112 and covering the coil with a polymer or ceramic material to isolate it from the surrounding environment (if necessary).

If the first method is utilized, a third substrate 160 is subjected to identical processing steps as that used in the creation of etched substrate 112. The resultant third substrate 160 presents a planar spiral coil 64 that does not protrude above the top of a recessed region 164. This arrangement is shown n FIG. 18. This substrate 160 is then aligned and temporarily bonded to the lower surface of substrate 112. Electrical contact with the third planar spiral coil 64 is made by laser rastering and/or chemical etching through the back side of the third substrate 160 to expose the back side of the coil. Then, electrically conductive material is deposited in the passage, thereby forming electrical feedthroughs 166. The manufacture of these feedthrough structures is detailed in co-pending U.S. patent application Ser. No. 11/314,046 filed Dec. 20, 2005, which application has previously been incorporated by reference. This step can take place at the substrate level or after the third substrate 160 is bonded to the first two substrates. Also, two or more feedthroughs can be provided as dictated by any additional electronics. This method for providing the third or external coil 164 is particularly desirable when the final device is intended to be implanted chronically in a patient, for it presents inductor coils which will not change position with respect to one another over very long periods of time, thereby minimizing a potential cause of drift within the sensor.

Figure 19:
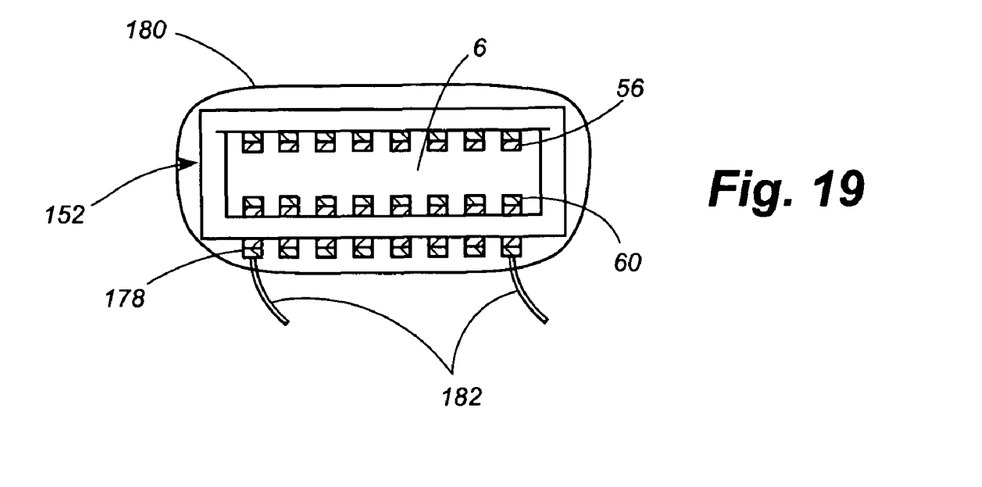
FIG. 19 is a cross-sectional view of a second embodiment of a sensor in which the sensor is encapsulated by a coating.
Figure 20:
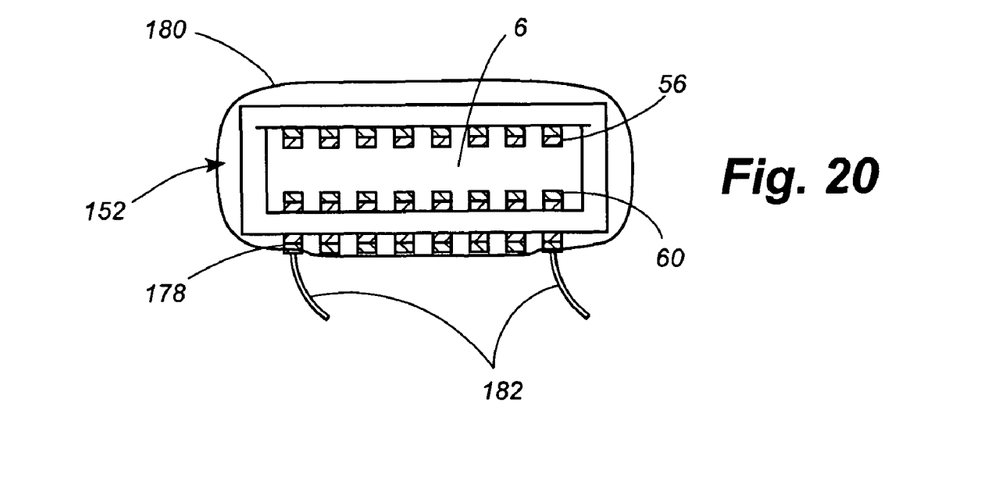
FIG. 20 is a cross-sectional view of a third embodiment of a sensor in which the sensor is substantially completely encapsulated by a coating.

Referring now to FIG. 19, if the second method is utilized, the first substrate 112 is subjected to additional photolithography and electrodeposition steps to create the third planar spiral coil 178 directly on the lower surface of the pressure cavity body 152. Then, at least the lower surface of the device, and optionally the entire sensor, is encapsulated in a polymeric material 180. Silicone rubber is a preferred material for this purpose. In this case, electrical contact of the third planar spiral coil 178 with external inductor leads 182 can be established before the polymer is applied via, e.g., conventional wire bonding techniques. Alternatively, the terminal ends of the coil can remain exposed or later be exposed, as shown in FIG. 20, to accomplish electrical contact subsequent to the application of the polymer coating.

Figure 21:
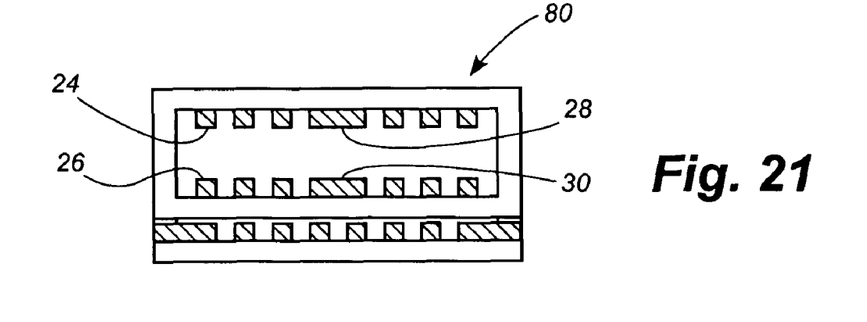
FIG. 21 is a cross-sectional view of a fourth embodiment of a sensor with an electromagnetically-coupled hermetic cavity according to the present invention.

FIG. 21 illustrates a sensor 80 that is a variation of the sensor 2 depicted in FIGS. 1 and 2. In FIG. 21 the sensor 80 comprises a first planar wire spiral coil 24 and a second planar wire spiral coil 26. The first spiral coil 24 terminates in a first electrode 28, and the second spiral coil 26 terminates in a second electrode 30. Here, electrodes, 28 and 30, are formed integral with the interior terminal ends of the planar spiral coils 24 and 26, respectively. The mutually-imposed electrodes 28, 30 form a "lumped" capacitor. The addition of this lumped capacitor serves to increase the capacitance and to shift the resonant frequency in a controllable manner. In a variation of this configuration, the planar spiral coils may be fixed so that they do not change position in response to changes in environmental pressure, thereby limiting the deflective region to at least one of the capacitor plates comprising the lumped capacitor. In this configuration, the inductance of the circuit is fixed, and the capacitance is variable.

Figure 22:
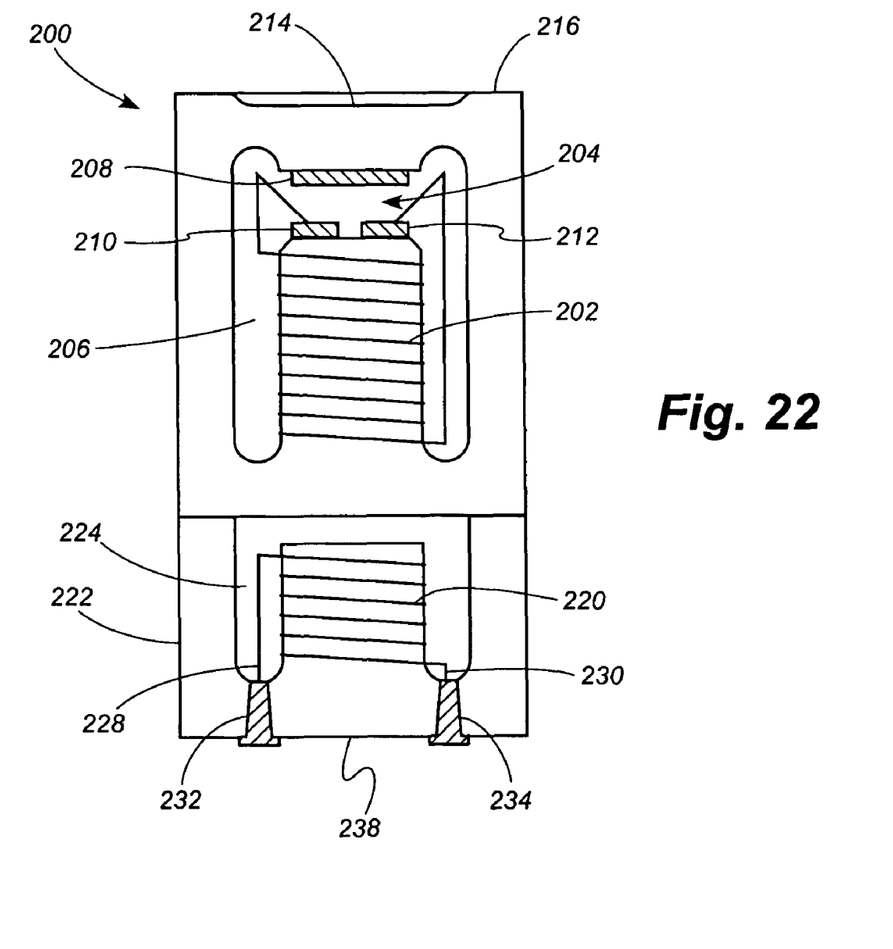
FIG. 22 is a cross-sectional view of a fifth embodiment of a sensor with an electromagnetically-coupled hermetic cavity according to the present invention.

Yet another sensor 200 according to the present invention is shown in FIG. 22. The sensor comprises an inductor 202 and a capacitor 204 housed within a hermetic chamber 206. In the sensor 200, the inductor 202 and capacitor 204 are arranged as a "lumped" LC circuit. In a lumped LC circuit, the inductor and the capacitor comprise two discrete elements. Thus, the inductance value of the circuit is substantially wholly attributable to a discrete inductor component while the capacitance value is substantially wholly attributable to a discrete capacitor component. It is a further aspect of this example that the inductor 202 comprises a three dimensional, helical coil structure, as opposed to the planar coil structure of the prior examples. Further, the capacitor comprises three capacitor plates, 208, 210, and 212. Either the inductor 202 or the capacitor 204 can be configured to vary in response to external pressure, although it is preferred that the capacitor be configured to do so. To this end, at least one capacitor plate 208 is fixed to a deflective region 214 on an upper substrate 216. The manufacture of the hermetic chamber 206 is detailed in co-pending U.S. patent application Ser. No. 11/157,375 filed Jun. 21, 2005, previously incorporated herein by reference. To modify the wireless sensor disclosed in the '375 application to the present invention, a second conductive structure comprising an external inductor coil 220 is provided.

In one aspect of this embodiment, a third substrate 222 is provided that comprises a trench 224 containing the external inductor coil 220. In this case, the coil leads 228, 230 are connected to electrical feedthroughs 232, 234 traversing the lower wall 238 of the third substrate 222. Bond pads can be provided for on the exterior surface of the device as a means to connect the sensor to other electronics. The manufacture of these feedthrough structures 232, 234 are detailed in co-pending U.S. patent application Ser. No. 11/314,046 filed Dec. 20, 2005, previously incorporated herein by reference.

Alternatively, the external inductor coil 220 can be attached directly to the lower surface of the sensor and encased in a stratum of polymeric material such as polyimide or silicone. In this case, the leads of the coil 220 can be utilized to attach the device to further electronics. Alternatively, separate wires can be connected to the coil 220, either before or after the coil has been encased in the polymeric material.

As an important note, the electrical resistance of the circuit is a function of the frequency of the final device. Thin film techniques and electroplating are two effective methods for creating the necessary metal traces comprising the circuitry. The metal deposition technique chosen should be capable of forming "thick" metal traces. The tendency for high-frequency currents to flow on the surface of a conductor is known as the "skin effect." Skin depth is the distance from the surface of the conductor at which the current flows and increases with decreasing frequency. The term "thick" as used herein should be construed to mean thick with regards to the skin depth of the metal at a frequency of interest. The relationship between skin depth and frequency is:

$$d = \frac{1}{\pi * f * \mu * \sigma}$$

where d is the skin depth, f is the frequency, $\mu$ is the magnetic permeability, and $\sigma$ is the electrical conductivity. Thus, the lower end of the desired range of frequency will determine the minimum skin depth of the wire used in construction of the circuit. If a wire thickness that is insufficient to accommodate the skin depth corresponding to the desired minimum frequency response is used, the resistance of the circuit will necessarily increase. Conversely, use of wire that is too thick needlessly increases the size of the inductor. Thus, the manufacturing technique chosen to form the metal traces comprising the circuit is selected with the above considerations in mind. (One exception is the case of the three dimensional inductor coils which are optionally constructed of pre-fabricated wire that is selected to have the appropriate thickness according to the above considerations.)

Figure 23:
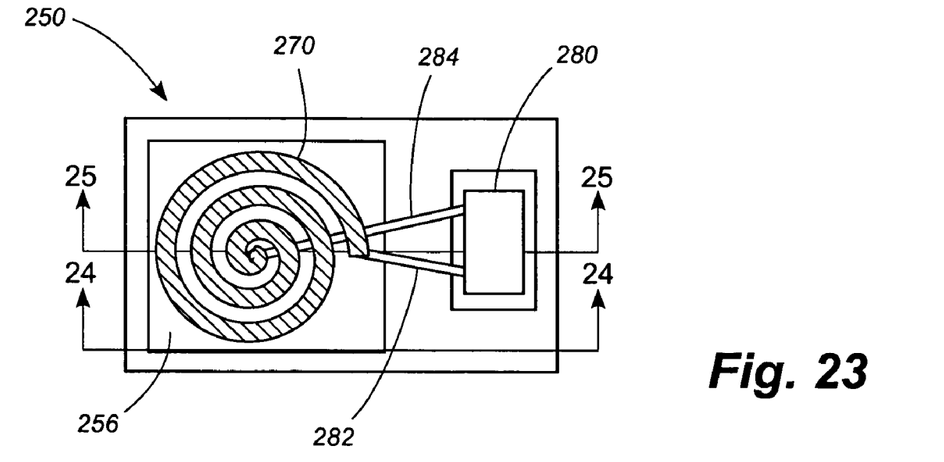
FIG. 23 is a cross-sectional view of a sixth embodiment of a sensor with an electromagnetically-coupled external cavity comprising additional electronics, taken along line 23-23 of FIG. 24.
Figure 24:
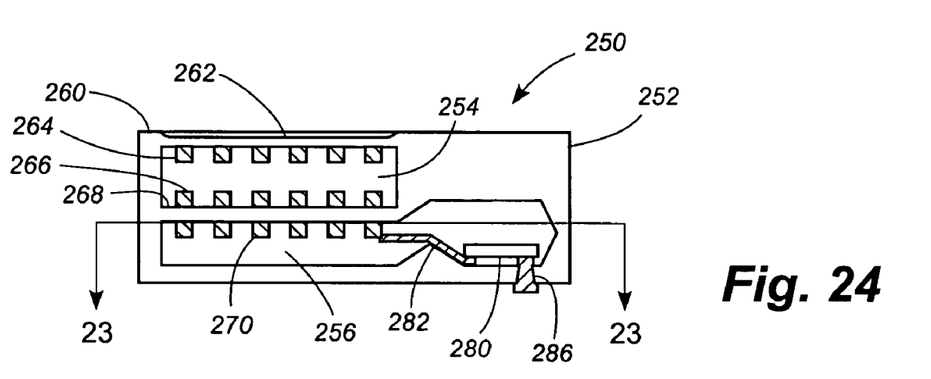
FIG. 24 is a cross-sectional view taken along line 24-24 of FIG. 23.
Figure 25:
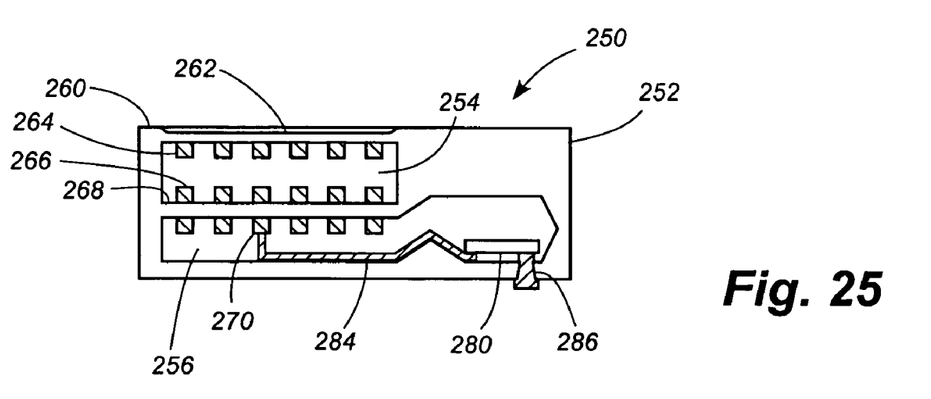
FIG. 25 is a cross-sectional view taken along line 25-25 of FIG. 23.

In any of the above embodiments, the external inductor coil can be attached to further electronics. For the purpose of illustration, a sensor 250 similar in principle to the sensor 2 of FIGS. 1 and 2 is shown in FIGS. 23-25 with additional electronics incorporated into the sensor package. The sensor 250 comprises a sensor body 252 defining a hermetic chamber 254 and a cavity 256. The upper wall 260 of the sensor body 252 comprises a deflectable region 262. An upper coil 264 is mounted within the hermetic chamber 254 to the lower side of the deflectable region. A lower coil 266 is mounted to the lower wall 268 of the hermetic chamber. An external coil 270 is mounted within the cavity 256 within magnetic proximity to the lower coil 266.

Additional electronics are mounted within the cavity 256 and comprise one or more silicon chips 280 bearing electronics. The additional electronics should be located sufficiently far away from the electromagnetic field to avoid any deleterious, parasitic interaction but should be close enough to preserve the small size of the device. It is possible for the additional electronics to be positioned vertically (not shown) or horizontally (as shown) relative to the inductor element. The leads 282, 284 of the inductor coil are placed in electrical communication with the silicon chip 280 via, e.g., conventional wire bonding techniques or by deposition of metal traces configured to provide conductive paths between the components. The silicon chip 280 is fixed in the cavity 256 either mechanically (e.g., press fit), with an adhesive (e.g., epoxy or polyimide), via use of flip chip interconnects, or via eutectic bonding using additional metallic interfaces (i.e., using soldered performs), or other methods known in the art. The silicon chip 280 can be placed in electrical communication with external electronics by way of feedthroughs 286.

One example of useful circuitry on the silicon chip 280 would be a high gain amplifier that causes oscillations at the natural resonant frequency of the arrangement of conductors 264, 266. In this approach, the output of the chip 280 consists of a frequency that depends on the external pressure. The geometry of the cavity needed to contain the electronics 280 and inductor coil 266 can be modified in various ways which are obvious to one skilled in the art.

It is also possible to contemplate positioning the silicon chip 280 within the hermetic chamber 254 instead of, or in addition to, the cavity 256. This may have advantages when a very high degree of compactness is required, and/or if the chip is required to operate in a hermetic environment with no direct feedthroughs. In this embodiment, electrical energy for chip operation can be supplied in a similar fashion to the energizing of conductors 268 and 264, with the addition of appropriate rectification and filtering circuitry on or adjacent to the chip 280 depending on the mode of energizing utilized.

Note that the sensors depicted above are all designed for maximum reliability because there are no conductor bonds or joints or feedthroughs breaching the hermetic cavity, and there are no wires connecting the two sides of the LC circuit contained within the pressure cavity. It is possible to provide a wire connecting the two sides of the LC circuit inside the pressure cavity to provide for DC coupling, but it is not necessary, and the absence of such a feature eliminates a potential site for failure of the device.

Specific embodiments have been described herein, by way of example and for clarity of understanding, and variations and modifications to the present invention may be possible given the disclosure above. Hence the scope of the present invention is limited solely by the appended claims.

I claim:

1. An apparatus comprising:
a monolithic body of substantial uniformity formed by thermal bonding defining a hermetic chamber having an upper wall and an opposed lower wall;
a first conductive structure disposed within said hermetic chamber, said first conductive structure comprising a distributed LC circuit, wherein a first portion of said distributed LC circuit is fixed to the upper wall of the chamber, and wherein a second portion of said distributed LC circuit is positioned oppositely disposed and substantially parallel to the first portion of said distributed LC circuit and is fixed to an upper surface of the lower wall of the chamber;
a second conductive structure fixedly disposed on a bottom surface of the lower wall outside said hermetic chamber in spaced, substantially parallel opposition to the second portion of said distributed LC circuit of said first conductive structure; and
means physically attached to the lower wall of said hermetic chamber for at least partially enclosing and isolating said second conductive structure;
wherein said first conductive structure is electromagnetically coupled to said second conductive structure without direct electrical paths connecting said first and second conductive structures.

2. The apparatus of claim 1, wherein the electrical characteristics of said first conductive structure are altered by variations in the geometry of the hermetic chamber; and wherein said apparatus further comprises means responsive to a change in an environmental parameter for varying the geometry of the hermetic chamber.

3. A sensor for indicating a physical state within a patient, comprising:
a monolithic sensor body of substantial uniformity formed by thermal bonding defining a hermetic chamber having an upper wall and a lower wall;
a first conductive structure disposed within said hermetic chamber and having an element providing an inductance, said first conductive structure comprising a distributed LC circuit, wherein a first portion of said distributed LC circuit is fixed to the upper wall of the chamber, and wherein a second portion of said distributed LC circuit is positioned oppositely disposed and substantially parallel to the first portion of said distributed LC circuit and is fixed to an upper surface of the lower wall of the chamber;
a second conductive structure fixedly disposed on a bottom surface of the lower wall outside said hermetic chamber in spaced, substantially parallel opposition to the second portion of said distributed LC circuit of said first conductive structure;
means physically attached to the lower wall of said hermetic chamber for at least partially enclosing and isolating said second conductive structure; and
means for connecting said second conductive structure to remote electronics disposed outside of said sensor body;
wherein there are no direct electrical paths connecting said first conductive structure disposed within said hermetic chamber to said second conductive structure disposed outside said hermetic chamber; and
wherein said second conductive structure can be excited using time-varying electrical excitation via said remote electronics and, subsequently, electromagnetically coupled to said first conductive structure disposed within said hermetic chamber.

4. The sensor of claim 3, wherein each of said first and second conductive structures comprise a capacitor.

5. The sensor of claim 3, wherein said first and second conductive structures comprise inductors.

6. The sensor of claim 3, wherein said body comprises ceramic material.

7. The sensor of claim 6, wherein said ceramic material is selected from the group consisting of glass, fused silica, sapphire, quartz, and silicon.

8. The sensor of claim 7, wherein said body comprises fused silica.

9. The sensor of claim 3, wherein a portion of said sensor body defining said hermetic chamber comprises a deflective region deflectable in response to a physiologically relevant pressure; and wherein at least a portion of said first portion of the distributed LC circuit of said first conductive structure is coupled to said deflective region.

10. The sensor of claim 3, wherein said first conductive structure disposed within said hermetic chamber provides a capacitance and an inductance.

11. The sensor of claim 3, wherein the distributed LC circuit of said first conductive structure further comprises: a first element providing an inductance; and a second element providing a capacitance, said first and second elements being electrically connected.

12. The sensor of claim 3, wherein said means for isolating at least a major portion of said second conductive structure from the ambient comprises a coating.

13. The sensor of claim 12, wherein said coating is selected from the group consisting of polyimide, liquid crystal polymer (LCP), urethane, polyester, Teflon, FEP, PTFE, polyamide and silicone rubber.

14. The sensor of claim 12, wherein said coating comprises silicone rubber.

15. The sensor of claim 3, wherein said means for connecting said second conductive structure to remote electronics disposed outside of said hermetic chamber comprises wires connected to said second conductive structure and extending through said means for isolating said second conductive structure from the ambient.

16. The sensor of claim 3, wherein said means for isolating at least a major portion of said second conductive structure from the ambient comprises ceramic material.

17. The sensor of claim 16, wherein said ceramic material is selected from the group consisting of glass, fused silica, sapphire, quartz, and silicon.

18. The sensor of claim 17, wherein said ceramic material is fused silica.

19. The sensor of claim 16, wherein said means for connecting said second structure to remote electronics comprises electrical feedthroughs disposed across said isolating means and coupled to said second structure.

20. The sensor of claim 3, wherein said second conductive structure is further connected to an integrated circuit.

21. The sensor of claim 3, wherein said means for isolating at least a major portion of said second conductive structure from the ambient comprises a cavity defined by said sensor body separate from said hermetic chamber.

22. The sensor of claim 21, wherein said integrated circuit is further coupled to electrical feedthroughs communicating between said second chamber and the ambient.

23. The sensor of claim 1, wherein said means physically attached to at least one of said walls defining said hermetic chamber for at least partially enclosing said second conductive structure comprises a coating physically contacting at least a portion of said at least one of said walls defining said hermetic chamber and at least partially encapsulating said second conductive structure.

24. The sensor of claim 1, wherein said means for at least partially enclosing said second conductive structure comprises a cavity defined by said sensor body separate from said hermetic chamber, and wherein said second conductive structure is disposed within said cavity.

25. The sensor of claim 1, wherein said means physically attached to at least one of said walls defining said hermetic chamber for at least partially enclosing said second conductive structure comprises means physically attached to at least one of said walls defining said hermetic chamber for completely enclosing said second conductive structure.

26. The sensor of claim 3, wherein said means physically attached to at least one of said walls defining said hermetic chamber for at least partially enclosing said second conductive structure comprises means physically attached to at least one of said walls defining said hermetic chamber for completely enclosing said second conductive structure.

27. The apparatus of claim 1, wherein the first portion of the distributed LC circuit of the first conductive structure comprises a first planar spiral coil, wherein the second portion of the distributed LC circuit of the first conductive structure comprises a second planar spiral coil, wherein the first and second planar spiral coils are disposed in parallel, spaced-apart relation.

28. The apparatus of claim 27, wherein the second conductive structure comprises a third planar spiral coil, and wherein the second and third spiral coils are disposed in parallel, spaced-apart relation.

29. The sensor of claim 3, wherein the first portion of the distributed LC circuit of the first conductive structure comprises a first planar spiral coil, wherein the second portion of the distributed LC circuit of the first conductive structure comprises a second planar spiral coil, wherein the first and second planar spiral coils are disposed in parallel, spaced-apart relation.

30. The sensor of claim 29, wherein the second conductive structure comprises a third planar spiral coil, and wherein the second and third spiral coils are disposed in parallel, spaced-apart relation.

* * * * *